(12) United States Patent
El-Hajal et al.

(10) Patent No.: US 11,048,100 B2
(45) Date of Patent: Jun. 29, 2021

(54) SYSTEM AND METHOD FOR OBTAINING OPHTHALMIC MEASUREMENTS FOR PROGRESSIVE LENSES THAT ACCURATELY ACCOUNT FOR BODY STATURE AND POSTURE

(71) Applicant: Optikam Tech, Inc., Montreal (CA)

(72) Inventors: Bassem El-Hajal, Montreal (CA); Marco Lancione, Montreal (CA); Piotr Szymborski, Montreal (CA); Luc Jalbert, Montreal (CA)

(73) Assignee: Optikam Tech, Inc., Montreal (CA)

( * ) Notice: Subject to any disclaimer, the term of this patent is extended or adjusted under 35 U.S.C. 154(b) by 258 days.

(21) Appl. No.: 16/387,091

(22) Filed: Apr. 17, 2019

(65) Prior Publication Data
US 2019/0324290 A1    Oct. 24, 2019

Related U.S. Application Data

(60) Provisional application No. 62/660,813, filed on Apr. 20, 2018.

(51) Int. Cl.
*G02C 7/02* (2006.01)
*A61B 3/11* (2006.01)
(Continued)

(52) U.S. Cl.
CPC .............. *G02C 7/027* (2013.01); *A61B 3/11* (2013.01); *G02C 7/06* (2013.01); *G02C 7/088* (2013.01); *G02C 13/003* (2013.01)

(58) Field of Classification Search
CPC .......... G02C 7/027; G02C 7/06; G02C 7/088; G02C 13/003; G02C 7/066; A61B 3/11
See application file for complete search history.

(56) References Cited

U.S. PATENT DOCUMENTS

| | | | |
|---|---|---|---|
| 6,257,721 | B1 | 7/2001 | Hayashi et al. |
| 7,033,023 | B2 | 4/2006 | Steele et al. |
| (Continued) | | | |

FOREIGN PATENT DOCUMENTS

| | | |
|---|---|---|
| EP | 1 038 495 | 9/2000 |
| FR | 2 896 682 | 8/2007 |
| (Continued) | | |

*Primary Examiner* — James C. Jones
(74) *Attorney, Agent, or Firm* — LaMorte & Associates, P.C.

(57) ABSTRACT

A method of obtaining ophthalmic measurements. An individual wears frames. Control simulations are performed to determine an average far gaze view line, average intermediate gaze view line, and average near gaze view line. The average far gaze view line intersects the lens plane at a second intersection point. The average intermediate gaze view line intersects the lens plane at a third intersection point. The average near gaze view line intersects the lens plane at a fourth intersection point. The far region extends from a first position above the first intersection point to a second position below the second intersection point. The intermediate region extends from the second position to a third position below the third intersection point. The near region extends from the third position to a fourth position below the fourth intersection point. The control simulation takes into account the height and stature to fit the natural viewing dynamic.

19 Claims, 7 Drawing Sheets

(51) Int. Cl.
*G02C 7/06* (2006.01)
*G02C 7/08* (2006.01)
*G02C 13/00* (2006.01)

(56) References Cited

U.S. PATENT DOCUMENTS

| | | |
|---|---|---|
| 9,057,886 B2 | 6/2015 | McCarty et al. |
| 9,110,309 B2 | 8/2015 | Sayag |
| 2013/0057825 A1 | 3/2013 | Kato |
| 2013/0215379 A1 | 8/2013 | Sayag et al. |
| 2015/0109578 A1 | 4/2015 | Baranton et al. |
| 2015/0185504 A1* | 7/2015 | Peloux .................. G02C 7/083 351/159.39 |
| 2015/0355480 A1 | 12/2015 | Contet et al. |

FOREIGN PATENT DOCUMENTS

| | | |
|---|---|---|
| FR | 2 898 193 | 9/2007 |
| FR | 2 931 002 | 11/2009 |

\* cited by examiner

SYSTEM AND METHOD FOR OBTAINING OPHTHALMIC MEASUREMENTS FOR PROGRESSIVE LENSES THAT ACCURATELY ACCOUNT FOR BODY STATURE AND POSTURE

RELATED APPLICATIONS

This application claims the benefit of U.S. Provisional Patent Application No. 62/660,813, filed Apr. 20, 2018.

BACKGROUND OF THE INVENTION

1. Field of the Invention

In general, the present invention relates to measurement systems and methods that are used to properly design and fit prescription eyewear. More particularly, the present invention relates to systems and methods that obtain ophthalmic measurements for fitting prescription eyewear with progressive lenses.

2. Prior Art Description

When a person gets a prescription for eyeglass lenses and selects a set of eyeglass frames, those lenses are not taken out of box, set into the frames, and handed to the customer. Rather, the lenses must be custom fabricated in a manner that takes into account the style of the selected eyeglass frames and the anatomical features of the person who will wear the eyeglass frames. When prescription lenses are fitted for a particular set of frames and for a particular person, several measurements must be made in order to ensure that the prescription lenses are fabricated properly. The needed measurements are commonly referred to as ophthalmic measurements in the industry. Many of the needed ophthalmic measurements depend solely upon the style and model of the eyeglass frames selected. Other ophthalmic measurements depend upon the anatomy of the person being fitted. Still other ophthalmic measurements depend upon how the eyeglass frames sit upon the face when being worn in a normal manner and how an individual looks through their eyewear lenses when performing various daily activities.

Obtaining proper ophthalmic measurements is particularly important when fitting eyeglasses with. progressive lenses. Progressive lenses are eyeglass lenses that are shaped to have different focal lengths for different regions of the lens. In this manner, a person can have corrected vision for various distances by looking through different regions of the lens. Progressive lenses are different from bifocal lenses because there are no distinct lines of separation between the different regions of the lens. Rather, the curvature of the lens progresses gradually from one region into another.

Referring to FIG. 1, a progressive lens 10 is shown. The progressive lens 10 has a far region 12 for viewing objects at a distance. The progressive lens 10 also has a near region 14 for viewing objects that are close, and an intermediate region 16 for viewing objects in between. The far region 12 and the near region 14 are joined by blending in the intermediate region 16. The blending creates smooth transitions among the changing curvatures that form the different focal lengths. An extended intermediate region 16 will provide a smoother transition than would a short intermediate region 16. An extended intermediate region 16 also provides a greater vertical field of view for intermediate objects.

The size, shape and position of the far region. 12, the near region 14 and the intermediate region 16 depend upon many factors that are derived from. taking proper ophthalmic measurements. However, there are deficiencies in the standard protocols used to take ophthalmic measurements. When taking ophthalmic measurements, lens fabricators instruct opticians to take measurements that reference a primary line of sight. The typical progressive lens is designed to have its far region below a primary line of sight that is calculated for the 'average' person, that is, an average person having an average stature and an average posture. Accordingly, measurements are taken that assume that the progressive lens will be worn at eye level at an average height above the ground and with a natural head tilt that produces a natural line of sight similar to the primary line of sight. This assumption is rarely true. The result is that many individuals with above-average stature and/or unusual postures are made to use progressive lenses with far, near, and intermediate regions that are improperly defined. This can force a person to view different objects at different distances through the wrong section of the progressive lens.

In this common scenario, the industry advises the patient go through an adaptation period where the patient must learn to look through an unnatural section of the progressive lens. Many people find this uncomfortable. As such, the progressive lenses are often not selected in favor of more traditional bifocal eyeglasses.

In the prior art, attempts have been made to adjust lens measurements to take into account the stature of the person wearing the eyeglasses. Such prior art systems are exemplified by U.S. Pat. No. 9,110,309 to Sayag. A problem associated with such prior art systems is that such systems may adjust for far viewing and near viewing, but the systems do not account for available space on the lens or the need for transition areas required between view zones. This often results in very narrow view zones or view zones that abruptly change and cause an image to skip as the eye passes between zones.

A need therefore exists for a method to better fit progressive lenses to people who have a body stature and/or posture that is not within the range of what is considered average. In this manner, individuals who are taller and shorter than average can utilize progressive lenses that are comfortable and better formed to the visual needs of the user. This need is met by the present invention as described and claimed below.

SUMMARY OF THE INVENTION

The present invention is a system and method of obtaining some ophthalmic measurements needed to fabricate progressive lenses for a person and for determining various magnification regions within the progressive lenses. The progressive lenses have different curvatures for a far region, an intermedicate region and a near region, in order to provide different magnifications when viewing objects at different distances.

An individual selects a set of eyeglass frames. The eyeglass frames have a lens plane and various physical dimensions for holding two progressive lenses. After selection, the individual wears the eyeglass frames so that certain other ophthalmic measurements can be determined. A measurement system is used to measure physiological dependent parameters, such as head tilt angle, pantoscopic tilt angle, and rear vertex distance.

A primary line of sight is determined for the person wearing the eyeglass frames, wherein the primary line of sight intersects the lens plane of the eyeglass frames at a first intersection point.

To determine the location of scope of the various magnification zones, control simulations are performed. During the control simulations, a person wearing the eyeglass frames views at least one object at different distances in order to determine an average far gaze view line, an average intermediate gaze view line, and an average near gaze view line. The average far gaze view line intersects the lens plane at a second intersection point. The average intermediate gaze view line intersects the lens plane at a third intersection point. Lastly, the average near gaze view line intersects the lens plane at a fourth intersection point.

A first magification range for the far region is set from a first position above the first intersection point to a second position below the second intersection point. A second magnification range for the intermediate region is set to extend from the second position to a third position below the third intersection point. Lastly, a third magnification range for the near region is set to extend from the third position to a fourth position below the fourth intersection point. Since the control simulation takes into account the height and stature of the individual, the different magnification ranges fit the natural viewing dynamic of the individual having the eyeglasses made.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention system and method can be used to create many different types of progressive lenses for different styles and models of eyeglass frames, only one exemplary embodiment of a progressive lens is illustrated and described. The exemplary embodiment selected sets forth one of the best modes contemplated for forming a progressive lens for a particular set of eyeglasses. The exemplary embodiment, however, is only meant to be an example and should not be considered a limitation when interpreting the scope of the appended claims.

Figure 1:
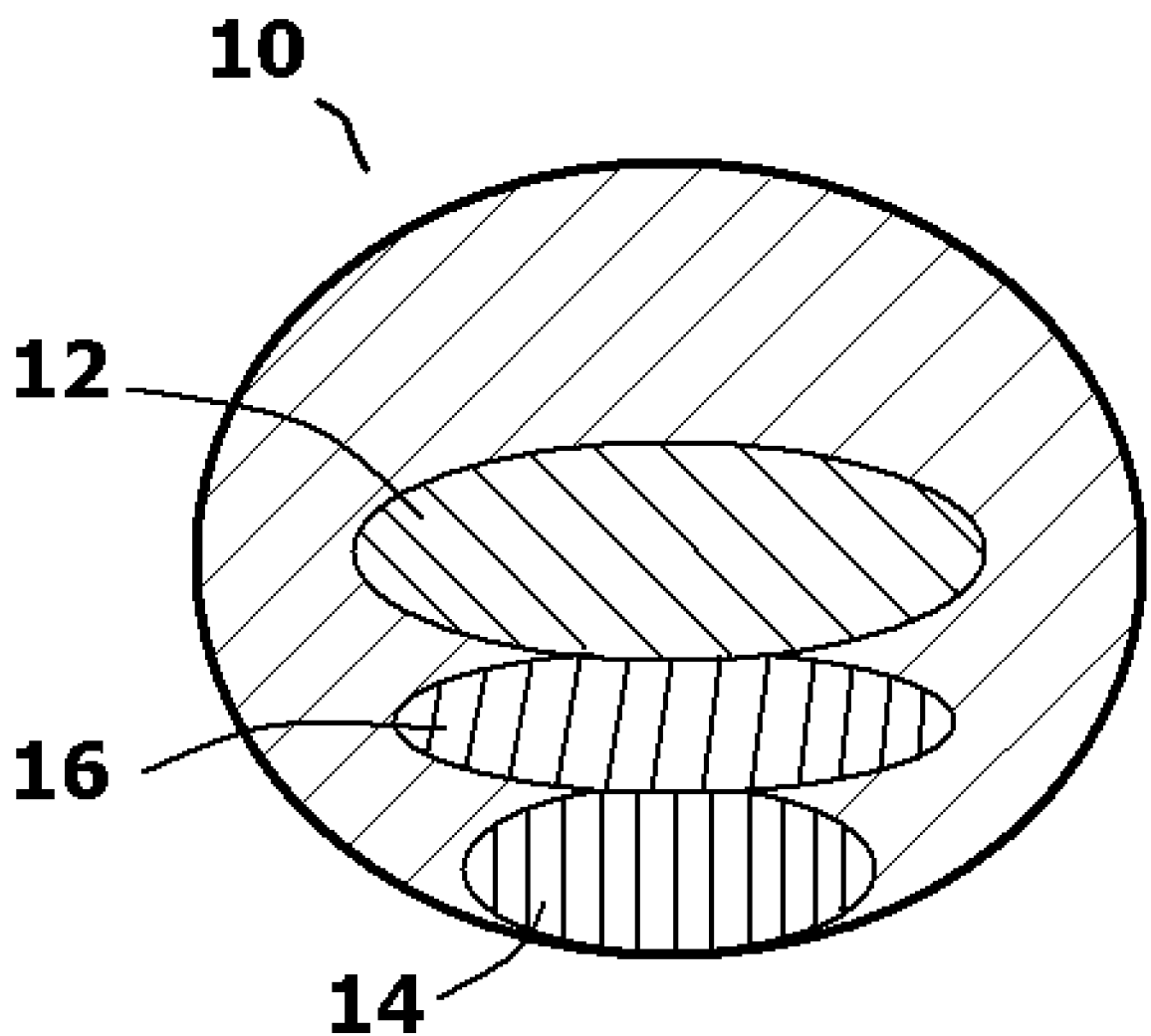
FIG. 1 shows the various focal regions on an exemplary progressive lens.
Figure 2:
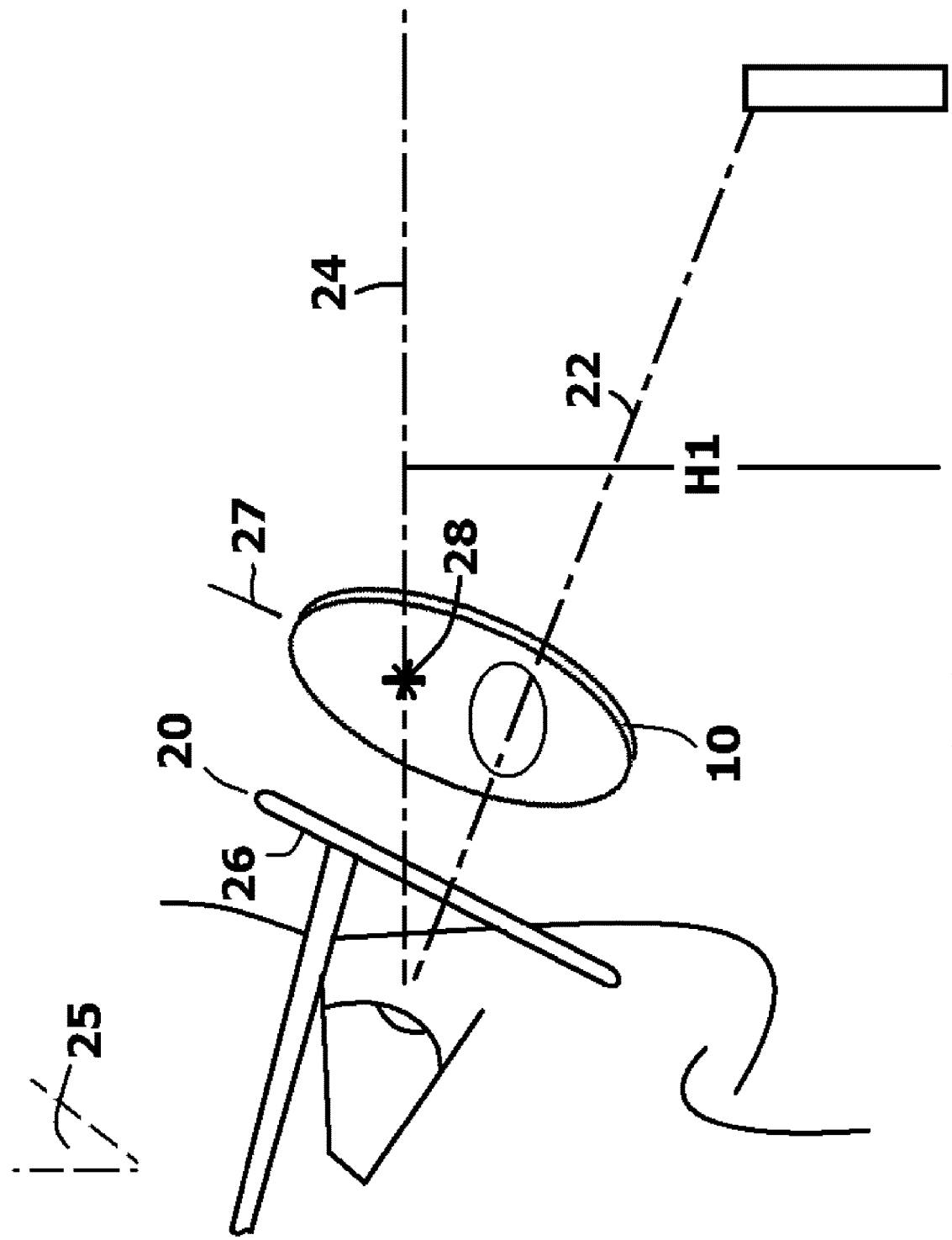
FIG. 2 shows a head wearing progressive lens eyeglasses, viewing an object, wherein the viewer has an average stature.

The present invention system and method is used to determine proper ophthalmic measurements needed to accurately fabricate progressive lenses, and how to use those measurements to create proper magnification regions for a person with unusual body stature and/or posture. Referring to FIG. 2, it can be seen that when a person wears eyeglasses 20, the orientation of the eyeglasses 20 is greatly affected by the posture of the person wearing the eyeglasses 20. Due to the natural posture of the body, nearly all people naturally hold their head slightly tilted forward at an angle 25. A typical head tilt angle 25 is between five and fifteen degrees. This is a large range that varies widely among individuals. Regardless of the head tilt angle 25, a person has a primary line of sight 24 that extends horizontally in front of the eyes. The head tilt angle 25, however, creates a natural line of sight 22 that is inclined downward. The natural line of sight 22 is perpendicular to the head tilt angle 25 and represents the natural resting position of person's eyes given their natural posture. As such, the natural line of sight 22 is angled downwardly from the horizontal at a complementary angle to the head tilt angle 25. Consequently, it will be understood that there is a difference between the natural line of sight 22 and the primary line of sight 24. This difference changes as a function of any change in the head tilt angle 25. The head tilt angle 25, in turn, changes in response to body movement during different activities. For example, when a person is walking, the head tilt angle 25 may be different from when that same person is sitting and viewing his/her mobile phone or driving in an automobile. As such, each person can be said to have many changing natural lines of sights, depending upon activity. These changing natural lines of sight can be averaged into a single natural line of sight 22.

When a person is fitted for a set of eyeglasses 20, that person typically selects the frames 26 for the eyeglasses 20. The frames 26 are then set on the face so that ophthalmic measurements can be taken. The current industry standard for taking ophthalmic measurements is to measure the head tilt angle 25 while a person is looking straight ahead. This will determine the natural posture of the person. The person is then told to look at a distant object, straight ahead, while maintaining their natural posture. This produces the primary line of sight 24. The location where the primary line of sight 24 passes through a lens plane 27 of the eyeglasses 20 is recorded as the fitting height. The fitting height is typically indicated by the use of a fitting cross 28. The fitting cross 28 is typically marked on mock lenses attached to the frames 26 for fitting purposes. In the prior art, the fitting cross 28 is used as a reference point, wherein the vertical field of view of the far region 12 of a progressive lens 10 is determined by setting the start of the intermediate region 16 between 2 mm and 4 mm below the fitting cross 28. This allows a person to have a gaze angle lower than the primary line of sight 24 while still viewing through the far region 12 of the progressive lens 10.

The primary line of sight 24 is not a good indicator of how an average person looks through the progressive lens 10 when moving about. When a person moves, they typically view their surroundings through a region of the progressive lens 10 that is close to their natural line of sight 22, that is, a line perpendicular to the natural posture head tilt angle 25. The natural line of sight 22 is related to where a person's eyes look naturally given their posture head tilt angle 25. This is how the eyes are naturally positioned, therefore this is the direction that the eyes view most. When a person moves, they change postures and use different gaze angles when looking at different objects. However, when viewing a far object, the disparity between the primary line of sight 24 and the natural line of sight 22 may cause a gaze angle to fall outside the far region 12 of the progressive lens 10, and therefore be out of proper focus. This is explained by comparing FIG. 2 to FIG. 3, as is explained below.

Figure 3:
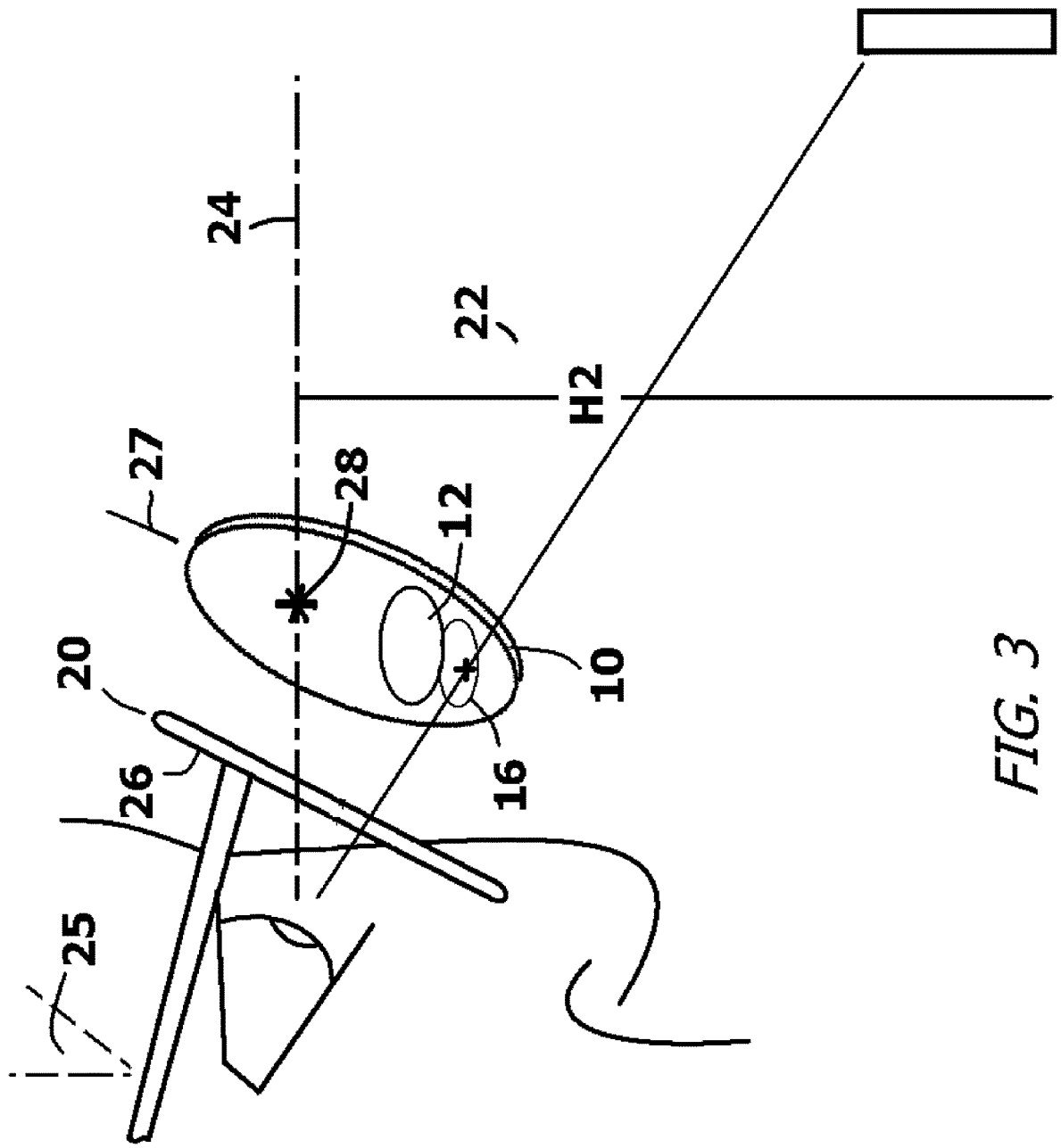
FIG. 3 shows a head wearing progressive lens eyeglasses, viewing an object, wherein the viewer has an above average stature.

FIG. 3 shows a person of a greater stature than the person shown in FIG. 2. In FIG. 3, the taller person has a primary line of sight 24 which is at a height H2 above the ground, which is greater than the height H1 of the shorter person in FIG. 2. Comparing FIG. 2 with FIG. 3, it will be understood that even assuming the shorter person and the taller person have the same head tilt angle 25, each person will naturally look below the primary line of sight 24 when walking. Due to human physiology, an average person focuses on objects that are about 1 meter high at a forward distance of between 3 meters and 10 meters, as they move forward. This assumption is utilized by most lens fabricators. However, lens fabricators also assume that the lens wearer will be a person of average height. The steeper gaze angle created by a taller person can cause a natural line of sight 22 to travel below the far region 12 of the progressive lens 10. This is because a taller person will have to look farther down, therein extending their natural line of sight 22 below the far region 12 of the progressive lens 10 and into the intermediate region 16. This results in a misfocus.

In the present invention, a height correcting methodology is utilized during the taking of ophthalmic measurements. If a person has an above-average stature and/or a high posture angle, i.e. tilt panto, then the corrective methodology appropriately lowers the measured fitting heights and extends the far region 12 of the progressive lens 10 to account for the natural line of sight 22 created by an above average height. As a consequence of lowering the fitting heights and expanding the far region 12, the near region 14 and/or the intermediate region 16 will get smaller. However, a near region 14 that is too small will make reading tasks more difficult. Additionally, a smaller intermediate region 16 will make the transition between the far region 12 and the near region 14 less gradual. This can result in abrupt changes in prism and magnification or 'image jump'. To provide more room for the expanded far region 12, a larger B-value frame (a frame with a higher lens height) is recommended.

Figure 4:
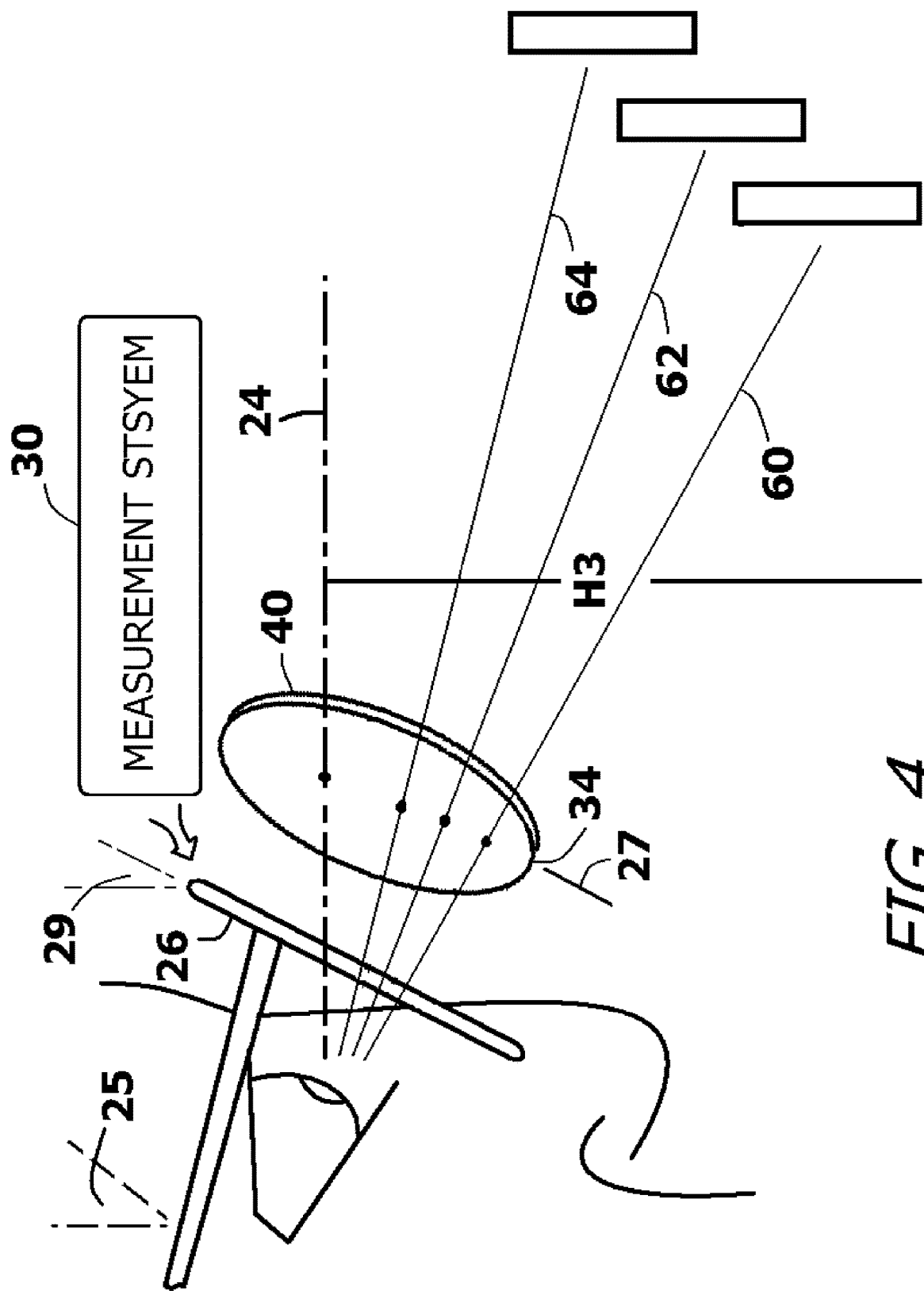
FIG. 4 shows a person wearing eyeglass frames and being measured by a measurement system to determine various ophthalmic measurements and various gaze view angles.
Figure 5:
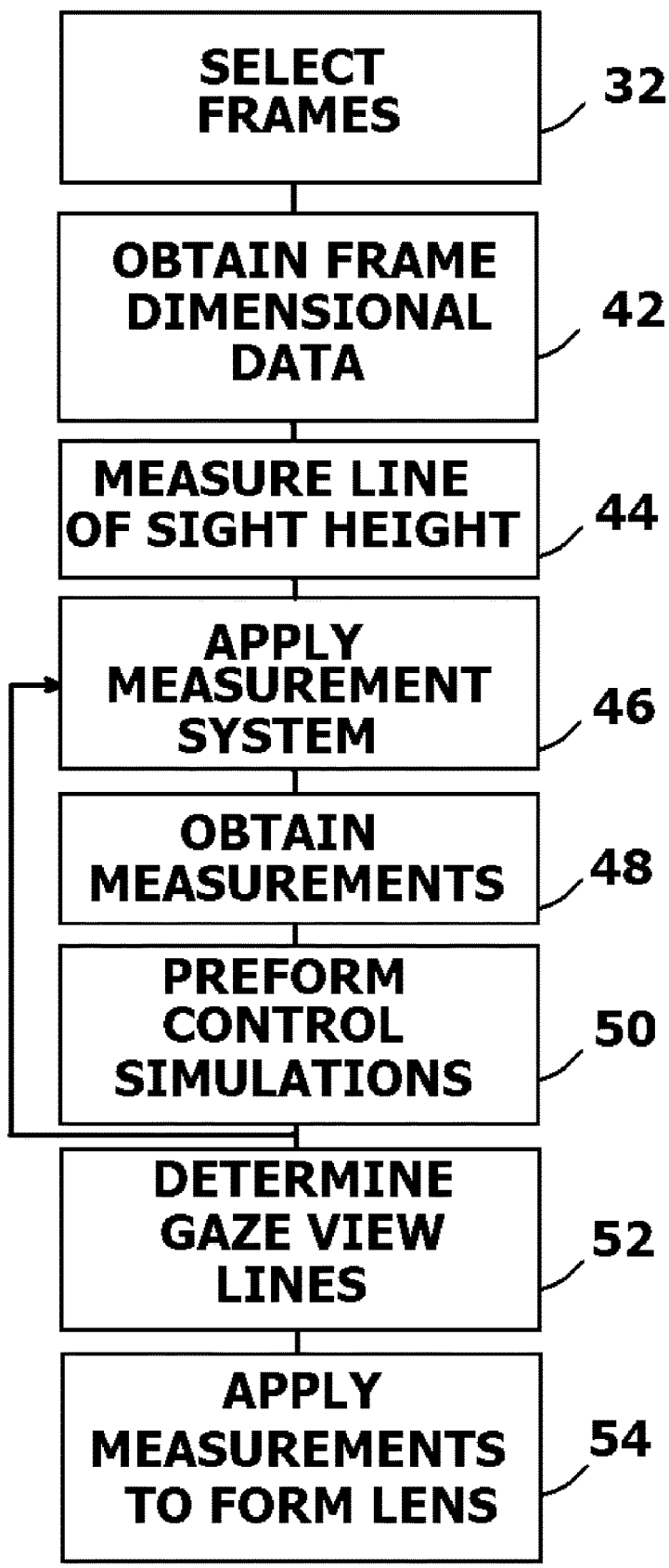
FIG. 5 is a block diagram showing the methodology of obtaining various ophthalmic measurements.

Referring to FIG. 4 in conjunction with FIG. 5, the methodology of the present invention is explained. In a first step, a person who wants progressive lenses selects a set of eyeglass frames 26. See Block 32. The eyeglass frames 26 must have a minimum lens height to accommodate a modified progressive lens. If the minimum lens height of the frames 26 cannot accommodate the various regions of the modified progressive lens 40, then more traditional bifocal or trifocal lenses must be used.

Once the eyeglass frames 26 are selected, certain ophthalmic measurements that correspond to the physical dimensions of the eyeglass frames 26 are obtained. See Block 42. For example, the lens opening length, lens opening height, effective diameters, datum line, frame length and distance between lenses can either be read from the specification data sheet of the eyeglass frames 26 or can be directly measured from the eyeglass frames 26.

In addition to obtaining dimensional data for the eyeglass frames 26, a measurement is taken for the height H3 of the person's primary line of sight 24. See Block 44. This measurement is taken while the person is relaxed and is embodying a normal head tilt angle 25. The point of intersection between the primary line of sight 24 and the lens plane 27 is no longer used as the primary reference point in determining the range of the different magnification regions, as is later explained.

For other ophthalmic measurements, a secondary measurement system 30 is supplied. See Block 46. The secondary measurement system 30 can be active or passive. An active measurement system has an electronic sensor unit or mechanical measurement instruments that directly attach to the eyeglass frames 20. A passive measurement system scans or images the user while wearing the eyeglass frames 20, wherein ophthalmic measurements are derived from the images. Active measurement systems are exemplified by U.S. Patent Application Publication No. 2018/0321517 and U.S. Pat. No. 8,820,921, both of which are owned by, or licensed to, the present applicant. Passive meaurement systems are exemplified by co-pending U.S. patent application Ser. No. 15/970,564 filed May 3, 2018 and co-pending U.S. patent application Ser. No. 15/853,703, filed Dec. 12, 2017, which are also owned by the present applicant. The disclosure of these secondary measurement systems are herein incorporated into this disclosure by reference.

The secondary measurement system 30 is used to obtain various ophthalmic measurements. See Block 48. The secondary measurement system 30 has the ability to measure the head tilt angle 25 relative to a vertical reference plane. The secondary measurement system 30 also measures a pantoscopic tilt angle 29, which is the lens plane angle as the frames 20 sit on the user's face. Other measurements that depend upon the anatomy of the person wearing the eyeglass frames 20 include, but are not limited to, pupil height, pupil distance, and rear vertex distance. The pupil height is the measured height of the pupils above a bottom edge 34 of the modified progressive lens 40. The rear vertex distance is the gap distance between the pupil and the modified progressive lens 40.

As the secondary measurement system 30 is used to collect ophthalmic measurements, the person wearing the eyeglass frames 20 is asked to participate in one or more control simulations. See Block 50. In a control simulation, a person is asked to view targets of known heights at known distances. A first control simulation is used to determine the person's field of view when looking at near objects. A second control simulation is used to determine a person's field of view when looking at intermediate objects. Lastly, a third control simulation is used to determine a person's field of view when looking at far objects. During the control simulations, it is important that the person wears the eyeglass frames 20 in the same manner as they would in real life. Likewise, the person places his/her body in the same position and holds his/her head in the same manner as they would in everyday life. The ophthalmic measurements taken during the control simulations are used to determine the average gaze view line for the person at near range, intermediate range, and far range. See Block 52. As such, after the control simulations, the average near gaze view line 60, the average intermediate gaze view line 62, and the average far gaze view line 64 become quantified by measurement.

From the measurement system 30, the rear vertex distance between the eye and the lens plane 27 is known, as is the head tilt angle 25 and the pantoscopic tilt angle 29. The intersection point 36 between the lens plane 27 and the primary line of sight 24 is also known. All these ophthalmic measurements are then applied in the fabrication of the modified progressive lens 40. See Block 52.

Figure 6:
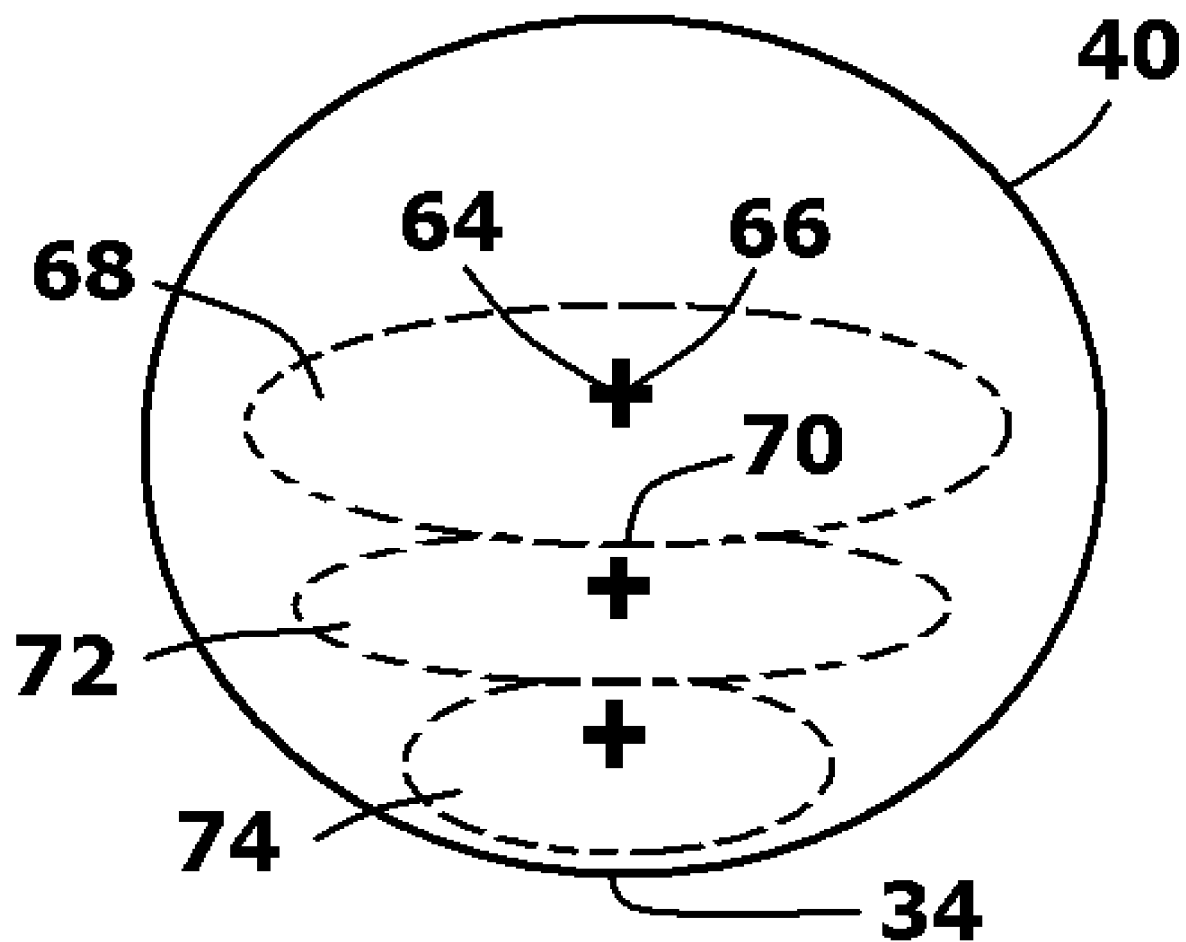
FIG. 6 shows a modified progressive lens created using the collected ophthalmic measurements.
Figure 7:
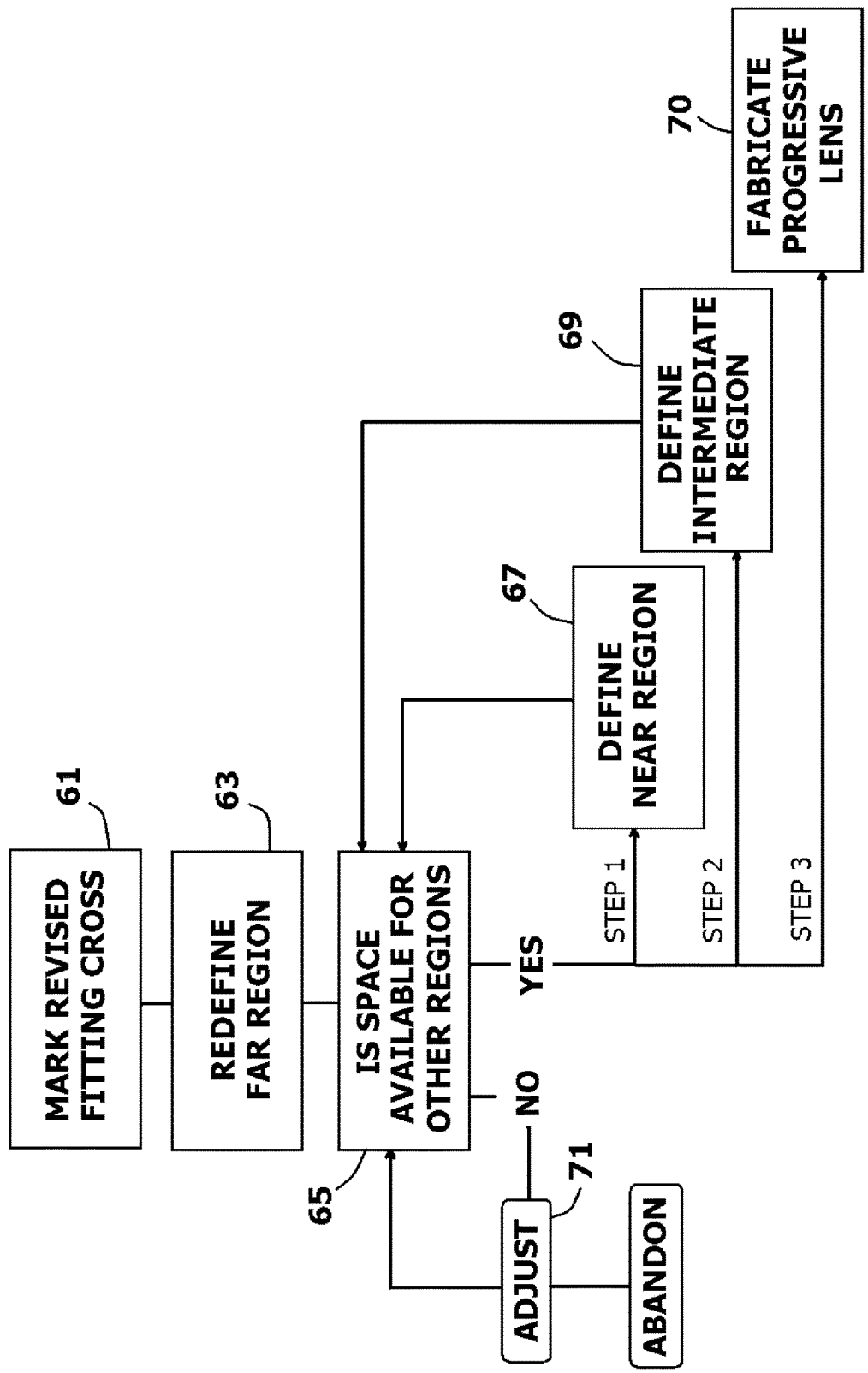
FIG. 7 is a block diagram showing the methodology used to obtain the different magnification regions used in FIG. 6.

Referring to FIG. 6 and FIG. 7, in conjunction with FIG. 4, it will be understood that a modified progressive lens 40 is made in the following manner. A revised fitting cross 66 is marked at the intersection point of the far gaze view line 64 and the lens plane 27. See Block 61. The far gaze view line 64 is conditioned on the height of the person and the head tilt angle 25 of the person. The second point of intersection is conditioned on the rear vertex distance and the pantoscopic tilt angle 29. As such, the location of the revised fitting cross 66 takes into account height variables that have previously been ignored in the fabrication of progressive lenses.

Using the revised fitting cross 66 as only a partial reference, the range of the new far region 68 of the modified progressive lens 40 is redefined. See Block 63. The size dimensions of the modified progressive lens 40 are known from the lens opening dimensions of the selected eyeglass frame 26. The distance between the revised fitting cross 66 and the bottom edge 34 of the modified progressive lens 40 is therefore known. A lower border 70 for the new far region 68 is set between 0.1 mm and 6 mm below the revised fitting cross 66. The distance between the lower border 70 and the revised fitting cross 66 can be no greater than one quarter the available distance between the bottom edge 34 of the modified progressive lens 40 and the revised fitting cross 66. This leaves three-quarters of the available distance for the placement of the new near region 74 and the new intermediate region 72 of the modified progressive lens 40.

A minimum height of four millimeters is preferred for the new near region 74 of the modified progressive len 40. This provides enough room for comforatable reading. Likewise, a mininum height of four millimeters is preferred for the new intermediate region of the modified progressive lens 40. If there is not enough room on the modified progressive lens 40 for the preferred minimums, adjustments are made. See Block 65. The adjustments are made in a multi-step process that follows the following order. First, the distance between the lower border 70 and the revised fitting cross 66 is reduced to make room for the new intermedicate region 72 and the new near region 74. This distance can be reduced until it is 1 mm in height. If there is still not enough room, the minimum height of the new intermediate region 72 and be reduced by 0.5 mm to 1.0 mm. If more room is required, the minimum height of the new near region 74 can be reduced by 0.5 mm to 1.0 mm. This is not optimal, but the disadvantages can be accepted by comsumers. See Block 67 and Block 69. If yet more room is required, the use of progressive lenses is abandoned in favor of more traditional bifocal lenses. See Block 71.

If there is room on the new progressive lens 40 for the new far region 68, the new intermediate region 72 and the new near region 74, the corresponding ophthalmic measurements are used to fabricate the eyeglasses 20. See Block 70. The results are eyeglasses 20 that are not only properly crafted for magnification, but are customized for the height and head tilt of the user.

It will be understood that the exemplary embodiment of the present invention system that is illustrated is merely exemplary and that many aspects of the system can be redesigned in manners that are functionally equivalent. All such variations, modifications and alternate embodiments are intended to be included within the scope of the present invention as claimed.

What is claimed is:

1. A method of obtaining some ophthalmic measurements needed to fabricate a progressive lens for a person, wherein said progressive lens has different curvatures for a far region, an intermediate region and a near region, said method comprising the steps of:
    selecting a set of eyeglass frames that has a lens plane;
    having the person wear said eyeglass frames;
    determining a primary line of sight for said person wearing said eyeglass frames, wherein said primary line of sight intersects said lens plane at a first intersection point;
    preforming control simulations where said person wearing said eyeglass frames views at least one object at different distances to determine an average far gaze view line, an average intermediate gaze view line, and an average near gaze view line, wherein said average far gaze view line intersects said lens plane at a second intersection point, said average intermediate gaze view line intersects said lens plane at a third intersection point, and said average near gaze view line intersects said lens plane at a fourth intersection point,
    determining a first range on said progressive lens to position said far region, wherein said first range extends from a first position above said first intersection point to a second position below said second intersection point;
    determining a second range on said progressive lens to position said intermediate region, wherein said second range extends from said second position to a third position below said third intersection point; and
    determining a third range on said progressive lens to position said near region, wherein said third range extends from said third position to a fourth position below said fourth intersection point.

2. The method according to claim 1, wherein said second range that extends from said second position to said third position extends at least four millimeters.

3. The method according to claim 2, wherein said third range that extends from said third position to said fourth position extends at least four millimeters.

4. The method according to claim 3, wherein selecting a set of eyeglass frames includes selecting said eyeglass frames with a lens height large enough to accommodate said first range, said second range and said third range.

5. The method according to claim 1, wherein said second position below said second intersection point is disposed between 0.1 millimeters and four millimeters below said second intersection point.

6. The method according to claim 1, wherein some of said ophthalmic measurements are obtained from physical dimensions associated with said eyeglass frames.

7. The method according to claim 6, wherein some of said ophthalmic measurements are obtained with measurements that reference both said eyeglass frames and said person wearing said eyeglass frames.

8. The method according to claim 7, further including attaching a measurement system to said eyeglass frames to obtain some of said ophthalmic measurements.

9. The method according to claim 7, further including scanning said person wearing said eyeglass frames with a measurement system to obtain some of said ophthalmic measurements.

10. A method of determining positions for magnification regions within a progressive lens, wherein said magnification regions include a far region, an intermedicate region and a near region, said method comprising the steps of:
    selecting a set of eyeglass frames that has a lens plane;
    having a person wear said eyeglass frames;
    performing control simulations where said person wearing said eyeglass frames views at least one object at different distances to determine an average far gaze view line, an average intermediate gaze view line, and an average near gaze view line, wherein said average far gaze view line intersects said lens plane at a first intersection point, said average intermediate gaze view line intersects said lens plane at a second intersection point, and said average near gaze view line intersects said lens plane at a third intersection point, determining a first range on said progressive lens to position said far region, wherein said first range extends from a first position above said first intersection point to a second position below said first intersection point;

determining a second range on said progressive lens to position said intermediate region, wherein said second range extends from said second position to a third position below said second intersection point; and determining a third range on said progressive lens to position said near region, wherein said third range extends from said third position to a fourth position below said third intersection point.

11. The method according to claim 10, further including determining a primary line of sight for said person wearing said eyeglass frames, wherein said primary line of sight intersects said lens plane at said first intersection point.

12. The method according to claim 10, wherein said second position below said first intersection point is disposed between one millimeter and four millimeters below said first intersection point.

13. The method according to claim 12, wherein said second range that extends from said second position to said third position extends at least four millimeters.

14. The method according to claim 13, wherein said third range that extends from said third position to said fourth position extends at least four millimeters.

15. The method according to claim 14, wherein selecting a set of eyeglass frames includes selecting said eyeglass frames with a lens height large enough to accommodate said first range, said second range and said third range.

16. The method according to claim 10, further including obtaining some ophthalmic measurements from physical dimensions associated with said eyeglass frames.

17. The method according to claim 16, further including obtaining some said ophthalmic measurements by referencing said eyeglass frames in relation to said person wearing said eyeglass frames.

18. The method according to claim 17, further including attaching a measurement system to said eyeglass frames to obtain some of said ophthalmic measurements.

19. The method according to claim 17, further including scanning said person wearing said eyeglass frames with a measurement system to obtain some of said ophthalmic measurements.

* * * * *